(12) United States Patent
Gamba et al.

(10) Patent No.: US 8,348,863 B2
(45) Date of Patent: Jan. 8, 2013

(54) RADICULAR SPECTRAL ATTENUATION COEFFICIENT FOR USE IN ENDODONTIC FORAMINAL LOCATOR

(75) Inventors: Humberto Remigio Gamba, Curitiba (BR); Ronaldo Piazzalunga, Londrina (BR); Joaquim Miguel Maia, Curitiba (BR); Carlos Alberto Spironelli Ramos, Londrina (BR); Alexandre Salcedo Ratzke, Curitiba (BR); Marcos Vinicius Haas Rambo, Curitiba (BR)

(73) Assignee: Ultradent Products, Inc., South Jordan, UT (US)

( * ) Notice: Subject to any disclaimer, the term of this patent is extended or adjusted under 35 U.S.C. 154(b) by 649 days.

(21) Appl. No.: 12/065,644

(22) PCT Filed: Feb. 9, 2006

(86) PCT No.: PCT/BR2006/000020
§ 371 (c)(1),
(2), (4) Date: Nov. 21, 2008

(87) PCT Pub. No.: WO2007/028217
PCT Pub. Date: Mar. 15, 2007

(65) Prior Publication Data
US 2009/0142726 A1    Jun. 4, 2009

(30) Foreign Application Priority Data
Sep. 6, 2005   (BR) ..................... 0504065

(51) Int. Cl.
*A61B 5/103* (2006.01)
*A61B 5/117* (2006.01)
*A61B 5/05* (2006.01)

(52) U.S. Cl. ...................... 600/590; 600/547
(58) Field of Classification Search ............ 600/590, 600/442, 502, 547; 433/81, 224
See application file for complete search history.

(56) References Cited

U.S. PATENT DOCUMENTS
4,629,424 A * 12/1986 Lauks et al. .............. 433/6
(Continued)

FOREIGN PATENT DOCUMENTS
BR    PI0504065-5    5/2007
(Continued)

OTHER PUBLICATIONS

HTTP://MATH.COM/TABLES/TRIG/HYPERBOLICS.HTM, Inverse Hyperbolic Definitions—arctanh(z), 2000-2005.*
(Continued)

*Primary Examiner* — Brian Szmal
*Assistant Examiner* — Mehari Kidanemariam
(74) *Attorney, Agent, or Firm* — Workman Nydegger

(57) ABSTRACT

The discovery of a new coefficient named "Radicular Spectral Attenuation Coefficient-RSAC", applicable in electronic foramen locators is described. The novelty is the use of the spectral attenuation of a multifrequency electrical current signal, applied through the endodontic file into the tooth canal (TC), to determine the root length and the foramen position. FIG. (2): (2.1), (2.4), (2.8) and (2.2), (2.5), (2.9) are the amplitude and frequency axes, respectively; (2.3) is the electrical current frequency spectrum applied into the TC; (2.6) shows the spectrum exponential decay (2.7) of the signal measured over the TC. In (2.10) the axes (2.4) and (2.5) were logaritmized to linearize the exponential decay. The RSAC is the average inclination of the line (2.11), which is proportional to the distance between the tip of the endodontic file and the apical foramen. The RSAC changes as the tip of the file gets near the foramen.

23 Claims, 3 Drawing Sheets

U.S. PATENT DOCUMENTS

| | | | |
|---|---|---|---|
| 5,096,419 A | | 3/1992 | Kobayashi |
| 5,211,556 A | * | 5/1993 | Kobayashi et al. ............. 433/72 |
| 5,295,833 A | | 3/1994 | Chihiro et al. |
| 5,449,000 A | * | 9/1995 | Libke et al. .................... 600/547 |
| 5,759,159 A | * | 6/1998 | Masreliez ...................... 600/547 |
| 6,059,569 A | * | 5/2000 | Otsuka ............................ 433/72 |
| 6,221,031 B1 | * | 4/2001 | Heraud ......................... 600/590 |
| 6,777,195 B2 | * | 8/2004 | Kozhemyakin et al. ..... 435/7.24 |
| 6,845,265 B2 | | 1/2005 | Thacker |
| 6,929,476 B2 | | 8/2005 | Katsuda et al. |
| 6,968,229 B2 | * | 11/2005 | Siemons ........................ 600/547 |
| 2002/0156399 A1 | * | 10/2002 | Kanderian et al. ............ 600/587 |

FOREIGN PATENT DOCUMENTS

| | | |
|---|---|---|
| WO | WO2007/028217 | 3/2007 |

OTHER PUBLICATIONS

Sedra et al., "Microelectronic Circuits," E-6 through E-8 (3rd Ed. 1991).

* cited by examiner

RADICULAR SPECTRAL ATTENUATION COEFFICIENT FOR USE IN ENDODONTIC FORAMINAL LOCATOR

TECHNICAL FIELD

The present invention is related to the discovery of a new coefficient called "Radicular Spectral attenuation Coefficient-RSAC" applicable in electronic foraminal locators to measure the root canal length and to locate the apical foramen, during the dental endodontic treatment.

STATE OF ART

One of the preliminary procedures in the endodontic treatment is to determine the root canal length (RCL) and the exact location of the apical foramen (LAF). The RCL is related to the deepest point the endodontic file may reach within the tooth root canal. The debridement and the canal filling cannot be performed unless the LAF is correctly determined and the canal completely cleaned.

Figure 1:
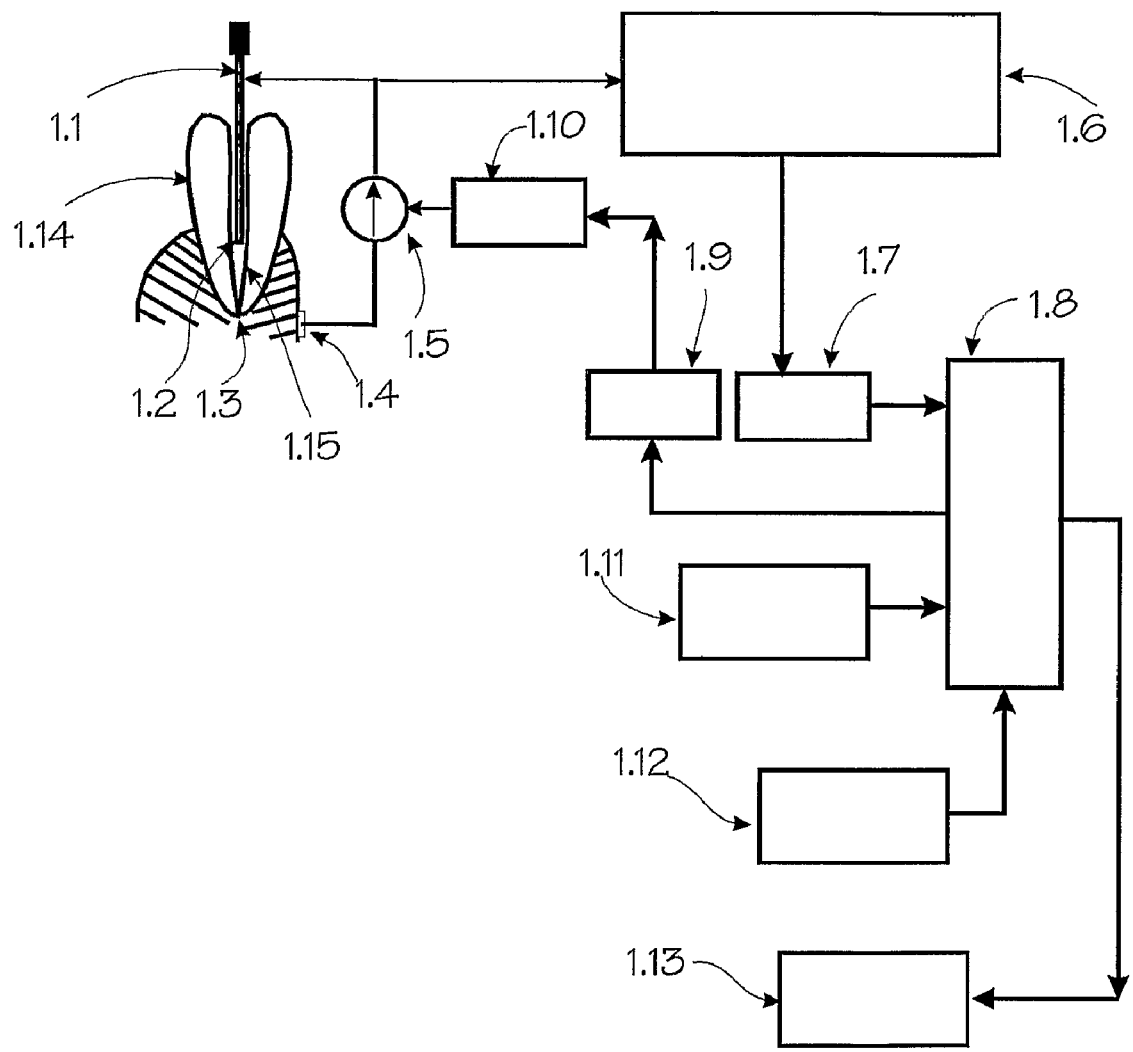

FIG. 1 presents an illustration of a tooth (1.14) with its radicular (1.15) canal opened. Within the radicular canal (1.15) it is inserted the endodontic file (1.1) used during the treatment of the tooth canal (1.14). There are two aims of a foraminal locator: determine the distance between the tip of the endodontic file (1.2) and the apical foramen (1.3); and to inform the dentist the exact point when the tip of the file has reached the foramen (1.3). The canal foramen (1.3) is the deepest anatomic point within the tooth canal that the endodontic file may reach during the treatment. That is, the LAF is extremely important for the success of the endodontic treatment. Therefore, the aim of our Radicular Spectral Attenuation Coefficient (RSAC) is to determine the root canal length and inform the dentist the exact point when the tip of the endodontic file reaches the apical foramen.

Until recently the RCL and the LAF were determined only by radiographic image. The main disadvantage of using radiographic images is that they produce a two-dimensional image of an object that has three-dimensions. Thus, the accurate determination of the RCL and the LAF is not always possible by radiography. Another drawback is the ionized radiation applied to the patient.

Electronic apex locators have been the subject of many U.S. patents, such as: U.S. Pat. Nos. 5,759,159; 5,211,556; 5,096,419; and 6,059,569. All these patens claim different physical principles to perform the task of locating the apical foramen of the tooth canal. Also, all these patents have in common the use of two electrodes: one electrode is inserted into the tooth root canal. In general this electrode is the endodontic file (1.1), and the other electrode is attached to the patient's lip (1.4). The aim is to determine the physical distance in millimeter between the tip of the endodontic file (1.2) and the apical foramen of the tooth canal (1.3).

The U.S. Pat. No. 5,759,159, Jun. 2, 1998, claims the use of a measurement signal with several different components of frequency. This signal is applied to the previously described electrodes. The complex impedance of the tooth canal is measured by the electronic system. For this, the system measures the amplitude in voltage between the electrodes (potential difference) and phases introduced in each frequency component. The amplitudes and phases are then mathematically combined and related with the distance between the tip of the endodontic file and the radicular foramen. At this point we must state that our RSAC, which is the aim of our patent, does not perform any phase measurement or combine amplitudes with phases to determine the RCL or the LAF.

The U.S. Pat. No. 5,211,556, issued May 18, 1993, claims a methodology of relating the decrease in the root canal resistance, as the tip of the measuring electrodes approaches the apical foramen, with the physical distance in millimeters between the tip of the inserted electrode (endodontic file) and the apical foramen. The resistance is measured through a measurement signal applied to the electrodes. A methodology to compensate the non-linearity of the measured resistance values, for different electrode position within the canal, is described. At this point we must state that our RSAC, which is the aim of our patent, does not measure resistance or impedances values to determine the RCL or the LAF.

The U.S. Pat. No. 5,096,419, Mar. 17, 1992, claims an apparatus to detect the apical position. In this patent a measurement signal with different frequencies is applied to the previously described electrodes. The ratio of the tooth canal impedance measured with different frequencies is calculated. The apical position is detected by monitoring the changes in the ratio value as the tip of the file gets near the apical foramen. According to the patent there is a significant change in this ratio when the tip of the endodontic file reaches the apical position. At this point we must state that our RSAC, which is the aim of our patent, does not calculate any ratio of impedances measured within the tooth canal with different frequencies.

The U.S. Pat. No. 6,059,569, issued May 9, 2000, describes an apical locator where two signals of alternating current with different frequencies are applied in the electrodes previously described. These two signals provide two current measurements that are logarithmically combined to indicate the foramen position. At this point we must state that our RSAC, which is the aim of our patent, does not measure electrical current that goes through the tooth root canal.

DESCRIPTION OF THE INVENTION

The origin of the idea for the new coefficient RSAC to measure the tooth canal length and to localize the apical foramen is based on the technique used to measure the ultrasound attenuation within the human tissue.

The technique for the ultrasound attenuation coefficient is called "Broadband Ultrasound Attenuation" or BUA. As the ultrasound propagates through the human tissue, its intensity decays exponentially with the distance. The BUA coefficient is determined by analyzing the logarithm of the ultrasound signal spectrum. Detailed explanation is beyond the scope of this patent. The fact is that resistors and capacitors circuits can be used to model the acoustic and electrical impedance of the tissues. Thus, we have visualized that a similar procedure, that is, the BUA measurement, is applicable to determine the tooth canal length and to localize the apical foramen.

Therefore, this patent of invention describes the discovery of a new coefficient called Radicular Spectral Attenuation Coefficient or RSAC. The RSAC is directly related with the distance between the tip of the endodontic file (1.2) and the radicular foramen (1.3). This distance is called Root Canal Length (RCL).

Thus, since the RSAC is directly related to the RCL, it also can be used as a reference for the localization of the radicular foramen (LRF). In the following paragraphs is described the physical principle involved with the RSAC measurement and how this coefficient is converted into the RCL and used as reference for the LRF The process of RSAC calculation is divided into three steps: 1) the application of a measurement signal; 2) the measurement of an electrical signal and from this signal the determination of the RSAC and 3) the conversion of the RSAC into the RCL and the LAF. The first two steps make use of the already described measurement electrodes (1.1) and (1.4).

The measurement signal, applied in the first step of the RSAC calculation, is composed of a sum of sine waves trigonometric functions, all them with the same amplitude but different frequencies (or periods) and initial phases. The measurement signal, represented by f(t), is determined by equation 1, $$f(t) = A \cdot \sum_{i=1}^{N} \sin(2 \cdot \pi \cdot f_i \cdot t + \varphi_i) \qquad (1)$$

where A is the sine waves amplitudes, $f_i$ is the $i^{th}$ component of frequency, π=3.14151617, $\phi_i$ is the sine wave phase shift of the $i^{th}$ component of frequency, sin is the trigonometric sine wave function, t represents the time and Σ is the sum of the sine waves with i varying from one to N. N is the number of sine waves used to generate f(t).

Figure 2:
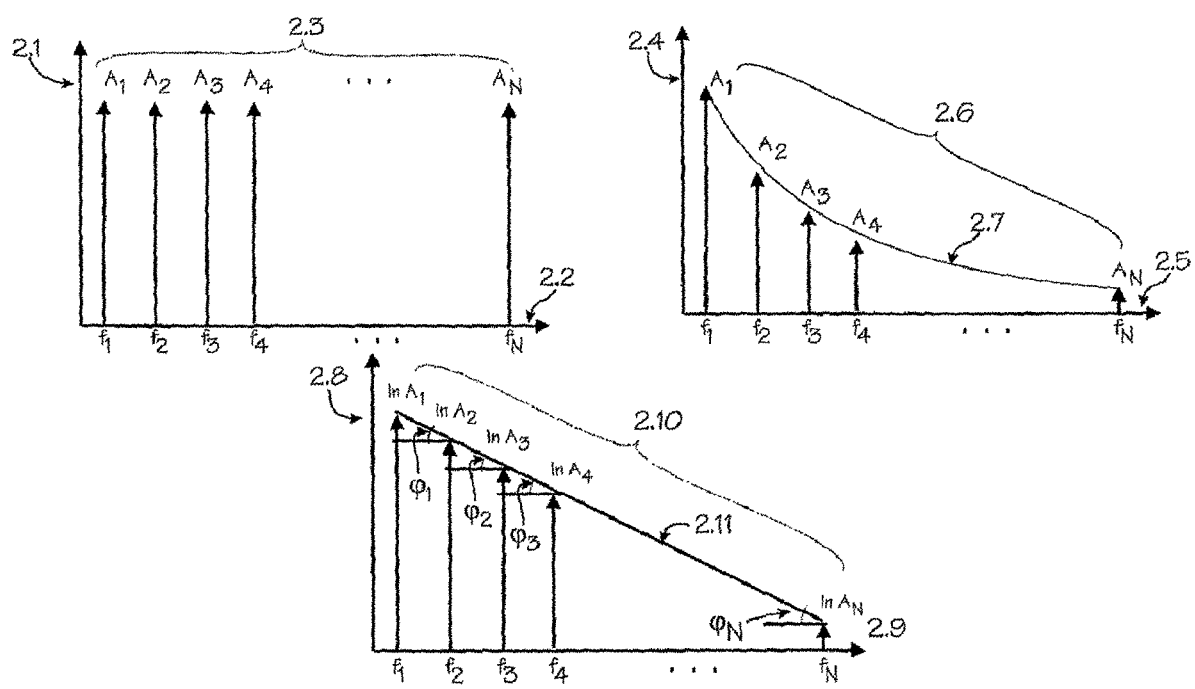

The f(t) signal spectrum is represented in FIG. 2. In FIG. 2 the axes (2.1) and (2.2) are the sine wave amplitude in volts and its frequency in cycles per second, respectively. The vertical arrows (2.3) are the N sine waves functions with frequencies $(f_1), (f_2), (f_3), \ldots, (f_N)$ that compose the measurement signal f(t). Note that all frequencies components (2.3) have the same amplitude value (A).

The signal f(t) is used to modulate or control a constant electrical current source. Thus, we have an electrical current signal whose waveform is the same for all N components of frequencies given by equation 1. The root mean square (RMS) value of the electrical current generated by the current source is below four micro-amperes and does not represent any risk for the patient or the surgery. The electrical current signal is applied to electrodes (1.1) and (1.4). This current circulates through the canal of the tooth and produces a potential difference between the electrodes (1.1) and (1.4).

The second step in the process of determining the RSAC is the process of measuring the potential difference between the electrodes (1.1) and (1.4). This potential difference has the same components of frequencies of the applied signal f(t). However, due to the electrical characteristics of the tooth canal, the frequency components of the applied signal (2.3) are attenuated differently. The spectrum of frequencies of the measured signal (potential difference between the electrodes (1.1) and (1.4)) is shown in figure (2.6). The length of the vertical arrows (2.6) represents the amplitude of each frequency component of the measured signal, indicated by $(A_1)$, $(A_2), (A_3), (A_4), \ldots (A_N)$. The axis (2.4) and (2.5) are the amplitudes in voltage and the frequency in Hz, respectively.

In a study performed by the inventors of this patent, it has been discovered that the attenuation of the frequency components (2.6) has a behavior very similar to an exponentional mathematical function. Thus, we have noticed that there is an exponentional attenuation (2.7) of the applied frequencies components (2.3). In an in vivo experiment, we notice also that the exponentional decay (2.7) changes as the file is introduced into the tooth canal.

The RSAC is determined by converting the axes scale (2.4) to a logarithm scale using the natural logarithm function. FIG. 2 illustrates the frequency spectrum, in which the axis (2.8) and (2.9) were logarithmized. In the logarithmized scale, the spectrum attenuation is a linear function (2.10). The RSAC is the line inclination, given by equation 2, $$RSAC = \tan^{-1}\left[\frac{\sum_{i=1}^{N-1}\left(\frac{|\ln(A_i) - \ln(A_{i+1})|}{|\ln(f_i) - \ln(f_{i+1})|}\right)}{N-1}\right] \qquad (2)$$

where $A_i$ e $A_{i+1}$ are the voltage amplitudes, $f_i$ and $f_{i+1}$ are the frequencies, ln is the natural logarithm, $\tan^{-1}$ is the arc tangent function, | | is the absolute value, Σ is the sum with i varying from one to N−1 and N is the number of frequency components used to generate f(t).

The third step in the measurement process is to convert the RSAC in the distance value between the tip of the endodontic file (1.2) and the apical foramen (1.3) in millimeter. This process is made through a calibration curve. This calibration curve is obtained from in vivo experiments.

FIG. 1 presents a block diagram of the implemented electronic circuit used to obtain the RSAC for the measurement of the RCL and in the LAF. The instrument makes use of a measuring electrode (1.1) that is inserted into the tooth canal and a clipping electrode (1.4) that is attached to the patient's lip or other oral soft tissue. A control unit (1.8), made with a micro-controller or microprocessor (1.8), executes the firmware (programme) stored in the microprocessor memory (1.12).

The measurement signal is the one previously described and given by equation 1. The measurement signal is then stored into memory (1.11). As the control unit (1.8) performs the memory addressing, the data stored in (1.11) is then sent to the digital-to-analog-D/A (1.9) and converted to voltage. The voltage at the output of the D/A (1.9) is then filtered by a low-pass-filter (1.10) to remove higher component of frequencies generated by the A/D and converted to an electrical current signal by a voltage-current source converter (1.5). The current signal is then applied to the measuring (1.1) and clipping (1.4) electrodes.

A potential difference between the electrodes (1.1) and (1.4) is then measured. This potential difference is amplified and filtered by the Signal Conditioner (1.6). After that, the signal is applied to analog-to-digital-A/D converter (1.7). The digitalized signal is then processed by the control unit (1.8), according to the firmware stored in (1.12). The result of the firmware process is then presented in the display (1.13).

Firmware Description

Figure 3:
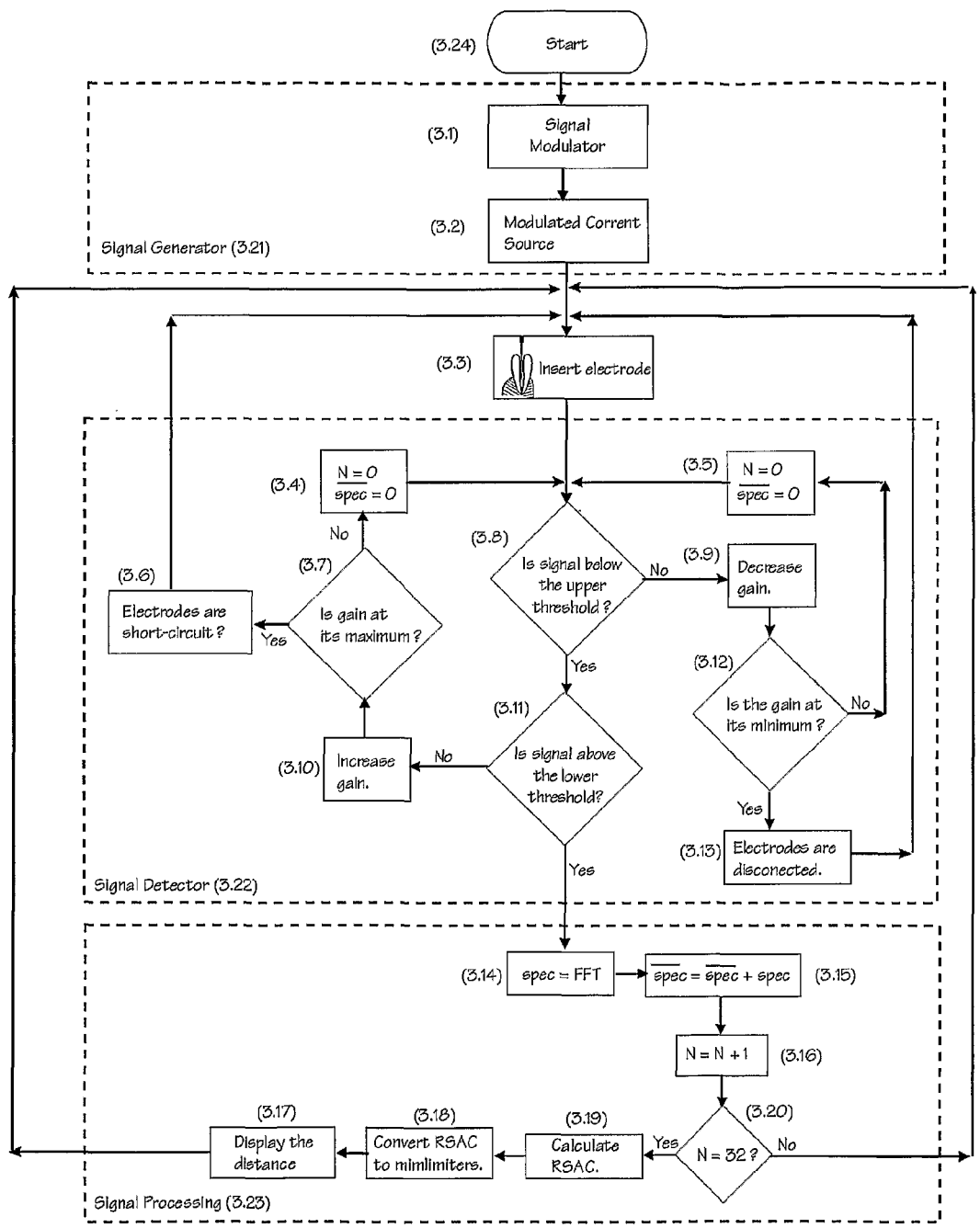

FIG. 3 presents a block diagram of the signal processing used to determine the RSAC, calculate the RCL and the LAF. The programme is divided into three parts: 1) Signal Generator (3.21); 2) Signal Detector (3.22) and 3) Signal Processing (3.23). The Signal Generator (3.21) has the Signal Modulator (3.1) whose signal is determined by equation 1. This signal is converted to electrical current by the Modulated Current Source (3.2). The instrument here described makes use of seven components of frequency (N=7): 500 Hz, 1 kHz, 2 kHz, 4 kHz, 8 kHz, 16 kHz and 32 kHz. Other components of frequency may be used, depending on the hardware capability, that is, faster processors allow the use of higher frequencies.

Next the amplitude of the measured signal is analyzed. This task is performed by the Signal Detector (3.22). The measured electrical signal (3.3), between the electrodes (1.1) and (1.4), must be between the upper (3.8) and lower (3.11) threshold values. If the measured signal is not below the upper threshold (3.8) the Gain Control (3.9) of the amplifier is automatically decremented. This gain is reduced (3.9) until the signal is below the upper threshold (3.8) and than it can be processed, or until the gain is at its minimal value (3.12). If the gain is at its minimal and the signal is still above the upper threshold, it is because the endodontic file is not inserted into the root canal (3.13) and it must be inserted for the measuring process be performed (3.3).

If the measured signal between the electrodes (1.1) and (1.4) is not above the lower threshold (3.11) the Signal Detector (3.22) automatically tries to increment the amplifier gain (3.10). The increase of the gain is performed until the measured signal amplitude is above the lower threshold, so it can be processed. On the other hand, if even with the amplifier set to its maximum gain (3.7) the signal is still below the minimum threshold, it is because the measuring electrodes are short-circuited (3.6).

Once the amplifier gain has been automatically set, the measured signal spectrum (spec) is calculated using a Fast Fourier Transform (FFT) algorithm (3.14). This procedure is repeated 32 times (counter (3.16)) for each calculated averaged. The average of 32 spectrum of the measured signal is calculated ((3.15), (3.16) and (3.20)) to improve the signal to noise ratio (SNR) of the measured signal. It is important to mention that the number of spectrum used to calculate the average may vary. In our studies, performed in vivo, the average of 32 acquisitions is enough to obtain a good SNR. Also, if for any reason (for instance, movement of the endodontic file), during the acquisition of the 32 signals used in the averaging process, there is a significant change in the amplifiers gain, the averaged is cancelled (3.4) and (3.5) and new signals are acquired.

Only after the average of 32 spectrum of the measured signal is calculated, the RSAC is computed (3.19) and its value converted into distance (3.18). After that the distance is then displayed (3.17).

Finally, it is important to emphasize that the RSAC is a new measurement coefficient discovered by us from in vivo experiments performed in patients, and it is completely different from any other method found in the literature.

The invention claimed is:

1. A method of determining a length of a radicular canal (RCL) of a tooth in a mouth and a location of an apical foramen (LAF) of the tooth using a Radicular Spectral Attenuation Coefficient (RSAC), comprising:
   introducing a first electrode into the radicular canal of the tooth;
   attaching a second electrode to oral tissue of the mouth;
   applying a measurement signal to the radicular canal of the tooth by means of the first and second electrodes, the measurement signal comprising at least 4 different frequencies, each frequency having an applied voltage amplitude;
   measuring an electrical signal and determining relative spectral attenuation of voltage amplitude of the measurement signal as a function of frequency in order to determine an individual attenuation of voltage amplitude for each frequency;
   determining, based on the relative spectral attenuation of the measurement signal as a function of frequency, the Radicular Spectral Attenuation Coefficient (RSAC); and
   deriving, from the Radicular Spectral Attenuation Coefficient (RSAC), the length of the radicular canal and location of a tip of an endodontic file relative to the apical foramen of the tooth.

2. A method as in claim 1, wherein the measurement signal includes at least the following components of frequency: 500 Hz, 1 kHz, 2 kHz, 4 kHz, 8 kHz, 16 kHz and 32 kHz.

3. A method as in claim 1, wherein the Radicular Spectral Attenuation Coefficient (RSAC) is determined according to the following equation:

$$RSAC = \tan^{-1}\left[\frac{\sum_{i=1}^{N-1}\left(\frac{|\ln(A_i) - \ln(A_{i+1})|}{|\ln(f_i) - \ln(f_{i+1})|}\right)}{N-1}\right]$$

where
   $A_i$ and $A_{i+1}$ are the attenuated voltage amplitudes measured for the plurality of frequencies,
   $f_i$ and $f_{i+1}$ are the frequencies,
   ln is the natural logarithm,
   $\tan^{-1}$ is the arc tangent function,
   | | is the absolute value,
   $\Sigma$ is the sum with i varying from one to N-1, and
   N is the number of frequency components used to generate f(t).

4. A method as in claim 1, wherein the measurement signal is comprised of an electrical current composed of at least the following frequency components: 500 Hz, 1 kHz, 2 kHz, 4 kHz, 8 kHz, 16 kHz and 32 kHz and is determined by the following equation:

$$f(t) = A \cdot \sum_{i=1}^{N} \sin(2 \cdot \pi \cdot f_i \cdot t + \varphi_i) \quad (1)$$

where A is the sine wave amplitude for each of the frequencies,
   $f_i$ is the $i^{th}$ component of frequency,
   $\pi = 3.14151617$,
   $\phi_i$ is the sine wave phase shift of the $i^{th}$ component of frequency,
   sin is the trigonometric sine wave function,
   t represents the time,
   $\Sigma$ is the sum of the sine waves with i varying from one to N, and
   N is the number of sine waves used in the measurement of the length of the radicular canal (RCL).

5. A method as in claim 1, wherein determining the Radicular Spectral Attenuation Coefficient (RSAC) comprises an average of 32 spectra of the measurement signal to improve the signal to noise ratio and improve localization of the apical foramen.

6. A method as in claim 1, wherein determining the Radicular Spectral Attenuation Coefficient (RSAC) comprises the use of N components of frequency, wherein N is at least 5.

7. A method as in claim 1, wherein the method comprises conversion of the RSAC into a distance between a tip of the first electrode and the apical foramen of the tooth.

8. A method as in claim 1, wherein the RSAC is converted into a distance between a tip of the first electrode and the apical foramen of the tooth using an empirically determined conversion curve.

9. A method as in claim 1, wherein the RSAC is determined without using values of electrical resistance.

10. A method as in claim 1, wherein the RCL and LAF are determined without using values of electrical resistance.

11. A method as in claim 6, wherein the value of N clinically assessed is at least 7.

12. A method as in claim 1, wherein the RSAC is determined without using values of electrical impedance applied to the tooth canal.

13. A method as in claim 1, wherein the RCL and LAF are determined without using values of electrical impedance applied to the tooth canal.

14. A method as in claim 1, wherein the RSAC is determined without using values of electrical current applied to the tooth canal.

15. A method as in claim 1, wherein the RCL and LAF are determined without using values electrical current applied to the tooth canal.

16. A method as in claim 1, wherein each of the plurality of frequencies has the same applied voltage amplitude.

17. A method as in claim 1, wherein the measurement signal has a waveform that includes components of all of the plurality of frequencies.

18. A method of determining a length of a radicular canal (RCL) of a tooth in a mouth and a location of an apical foramen (LAF) of the tooth using a Radicular Spectral Attenuation Coefficient (RSAC), comprising:
   introducing a first electrode into the radicular canal of the tooth;
   attaching a second electrode to oral tissue of the mouth;
   applying a measurement signal to the radicular canal of the tooth by means of the first and second electrodes, the measurement signal having a plurality of frequencies, including frequencies below 4 kHz and frequencies above 4 kHz, each frequency having an applied voltage amplitude;
   measuring an electrical signal and determining relative spectral attenuation of the voltage amplitude of the measurement signal as a function of frequency in order to determine an individual attenuation of voltage amplitude for each frequency;
   determining, based on the relative spectral attenuation of the measurement signal as a function of frequency, the Radicular Spectral Attenuation Coefficient (RSAC); and
   deriving, from the Radicular Spectral Attenuation Coefficient (RSAC), the length of the radicular canal and location of a tip of an endodontic file relative to the apical foramen of the tooth.

19. A method as in claim 18, wherein the measurement signal includes at least the following components of frequency: 500 Hz, 1 kHz, 2 kHz, 4 kHz, 8 kHz, 16 kHz and 32 kHz.

20. A method as in claim 18, wherein the measurement signal has a waveform that includes components of all of the plurality of frequencies.

21. A method of determining a length of a radicular canal (RCL) of a tooth in a mouth and a location of an apical foramen (LAF) of the tooth using a Radicular Spectral Attenuation Coefficient (RSAC), comprising:
   introducing a first electrode into the radicular canal of the tooth;
   attaching a second electrode to oral tissue of the mouth;
   applying a measurement signal to the radicular canal of the tooth by means of the first and second electrodes, the measurement signal having a plurality of frequencies and a waveform that includes components of all of the plurality of frequencies, each frequency having an applied voltage amplitude that equals a voltage amplitude of every other frequency;
   measuring an electrical signal and determining relative spectral attenuation of the voltage amplitude of the measurement signal as a function of frequency in order to determine an individual attenuation of voltage amplitude for each frequency;
   determining, based on the relative spectral attenuation of the measurement signals as a function of frequency, the Radicular Spectral Attenuation Coefficient (RSAC); and
   deriving, from the Radicular Spectral Attenuation Coefficient (RSAC), the length of the radicular canal and location of a tip of an endodontic file relative to the apical foramen of the tooth.

22. A method as in claim 21, wherein the measurement signals include frequencies ranging from 500 Hz to at least 32 kHz.

23. A method as in claim 18, wherein the measurement signals include at least the following components of frequency: 500 Hz, 1 kHz, 2 kHz, 4 kHz, 8 kHz, 16 kHz and 32 kHz.

* * * * *